United States Patent

Rainey et al.

[11] 3,965,107
[45] June 22, 1976

[54] ISOTHIAZOLOPYRIDINONES

[75] Inventors: James L. Rainey, Abington; Michael C. Seidel, Chalfont, both of Pa.

[73] Assignee: Rohm and Haas Company, Philadelphia, Pa.

[22] Filed: July 8, 1974

[21] Appl. No.: 486,550

[52] U.S. Cl. ................ 260/294.8 C; 260/247.1 H; 260/293.57; 424/256; 424/248; 424/267; 71/91
[51] Int. Cl.² ..................................... C07D 513/04
[58] Field of Search .............. 260/294.8 C, 293.57, 260/247.1 H

[56] References Cited
OTHER PUBLICATIONS
Fischer et al., "Arzneimittel-Forsch," vol. 14, No. 12, pp. 1301–1306 (1964).

*Primary Examiner*—Henry R. Jiles
*Assistant Examiner*—Robert T. Bond
*Attorney, Agent, or Firm*—Betty A. Narducci

[57] ABSTRACT

This invention relates to novel isothiazolopyridinones of the formula:

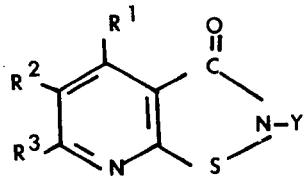

wherein Y is hydrogen, $(C_1-C_{12})$alkyl, aralkyl of up to 11 carbon atoms, $(C_1-C_4)$alkylcarbonyl, $(C_6-C_{10})$arylcarbonyl, aralkyl-carbonyl of up to 11 carbon atoms, $(C_2-C_3)$hydroxyalkyl, a group of the formula:

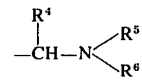

wherein $R^4$ is hydrogen, $(C_1-C_4)$alkyl or phenyl and $R^5$ and $R^6$ are individually $(C_1-C_4)$alkyl or taken together with the nitrogen atom to which they are attached, form a 5 or 6 membered azacyclic ring, which can include as additional hetero atoms, O, S or N or any combination of these wherein the total number of hetero atoms does not exceed 3; or a carbamoyl group of the formula:

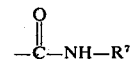

wherein $R^7$ is $(C_1-C_{18})$alkyl, $(C_6-C_{10})$aryl or aralkyl of up to 11 carbon atoms; $R^1$ and $R^3$ are individually hydrogen, $(C_1-C_4)$alkyl, phenyl or benzyl; and $R^2$ is hydrogen or $(C_1-C_4)$alkyl; provided that at least one of $R^1$, $R^2$ and $R^3$ is other than hydrogen; to agricultural compositions containing them, to processes for preparing them and to their utilization in controlling phytopathogenic fungi.

18 Claims, No Drawings

ISOTHIAZOLOPYRIDINONES

This invention relates to novel substituted isothiazolopyridinones, to agricultural compositions containing them, to processes for preparing them and to their utilization in controlling phytopathogenic fungi. The novel compounds of the present invention can be represented by the formula:

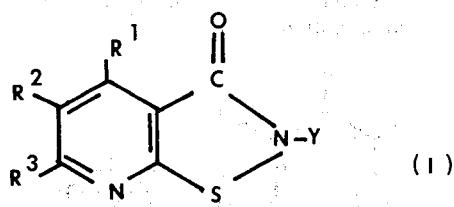

(I)

wherein Y is hydrogen; $(C_1-C_{12})$ alkyl, preferably $(C_1-C_8)$ alkyl, most preferably $(C_1-C_4)$ alkyl; $(C_1-C_4)$ alkylcarbonyl; $(C_6-C_{10})$ arylcarbonyl, preferably benzoyl; aralkylcarbonyl of up to 11 carbon atoms, preferably benzylcarbonyl; $(C_2-C_3)$hydroxyalkyl; a group of the formula:

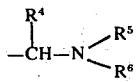

wherein $R^4$ is hydrogen, $(C_1-C_3)$ alkyl or phenyl, and $R^5$ and $R^6$ are individually $(C_1-C_4)$alkyl or taken together with the nitrogen atom to which they are attached, form a 5 or 6 membered azacyclic ring, which can include as additional hetero atoms, O, S or N or any combination of these wherein the total number of hetero atoms does not exceed 3; or a carbamoyl group of the formula:

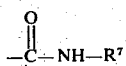

wherein $R^7$ is $(C_1-C_{18})$alkyl, preferably $(C_1-C_8)$alkyl, most preferably $(C_1-C_4)$alkyl; $(C_6-C_{10})$aryl, preferably phenyl; or aralkyl of up to 11 carbon atoms, preferably benzyl; $R^1$ and $R^3$ are individually hydrogen; $(C_1-C_4)$alkyl, preferably methyl; phenyl or benzyl; $R^2$ is hydrogen or $(C_1-C_4)$alkyl, provided that at least one of $R^1$, $R^2$ and $R^3$ is other than hydrogen; and strong acid salts of these compounds wherein Y is hydrogen or $(C_1-C_{12})$alkyl.

As used in the specification and claims, the term "alkyl" is intended to include straight chain as well as branched chain alkyl groups. Representative alkyl groups include methyl, butyl, isobutyl, pentyl, octyl, t-octyl, octadecyl and the like.

The term "aryl" is intended to include unsubstituted aryl groups, such as phenyl and naphthyl, as well as such aryl groups having one or more of the hydrogen atoms on the aryl ring replaced by another substituent group. Examples of such substituent groups include halogen, cyano, nitro, $(C_1-C_4)$alkoxy, $(C_1-C_6)$alkyl, and the like.

The term "aralkyl" is intended to include unsubstituted aralkyl groups, such as benzyl and naphthalenylmethyl, as well as substituted aralkyl groups having one or more of the hydrogen atoms replaced by another substituent group. Examples of the substituted aralkyl groups which characterize the isothiazolopyridinones of this invention include halogen-, cyano-, nitro-, $(C_1-C_4)$alkoxy or $(C_1-C_6)$ alkyl-substituted aralkyl groups, and the like.

The term "azacyclic ring" is intended to include unsubstituted azacyclic rings, such as pyridine and morpholine, as well as such azacyclic rings having one or more of the hydrogen atoms on the ring replaced by another substituent group such as halogen, cyano, nitro, $(C_1-C_4)$alkoxy, $(C_1-C_6)$alkyl, and the like.

Representative Y substituents include methyl, propyl, isobutyl, pentyl, hexyl, heptyl, t-octyl, dodecyl, benzyl, 3-bromobenzyl, 2,5-dimethylbenzyl, 3,4-dichlorobenzyl, 4-butylbenzyl, naphthalenylmethyl, 4-phenylbutyl, methylcarbonyl, isopropylcarbonyl, benzoyl, 3,4-dibromobenzoyl, 4-methoxybenzoyl, 2,5-dimethylbenzoyl, naphthoyl, 3-phenyl-propylcarbonyl, hydroxyethyl, hydroxypropyl, diethylaminomethyl, dimethylamino (phenyl) methyl, piperidinomethyl, morpholinomethyl, methylcarbamoyl, octylcarbamoyl, octadecylcarbamoyl, phenylcarbamoyl, 4-methylphenylcarbamoyl, 2,5-diethylphenylcarbamoyl, 4-chlorophenylcarbamoyl, 3,4-dibromophenylcarbamoyl, 4-nitrophenylcarbamoyl, 4-methoxyphenylcarbamoyl, naphthylcarbamoyl, benzylcarbamoyl, 4-chlorobenzylcarbamoyl and the like.

In a preferred embodiment of this invention, $R^1$ and $R^3$ are methyl groups, $R^2$ is a hydrogen atom and Y is a hydrogen atom, a methyl group or a phenylcarbamoyl group.

Typical compounds within the scope of this invention include:
isothiazolo-(5,4-b)-4,6-dimethylpyridin-3(2H)-one
isothiazolo-(5,4-b)-5-methylpyridin-3(2H)-one
isothiazolo-(5,4-b)-4,6-diethylpyridin-3(2H)-one
isothiazolo-(5,4-b)-6-isobutylpyridin-3(2H)-one
isothiazolo-(5,4-b)-6-isobutylpyridin-3-one hydrochloride
2,4,6-trimethylisothiazolo-(5,4-b)-pyridin-3-one
2,5,6-trimethylisothiazolo-(5,4-b)-pyridin-3-one
2-methylisothiazolin-(5,4-b)-6-isobutylpyridin-3-one
2-propylisothiazolin-(5,4-b)-6-isobutylpyridin-3-one
2-isopropylisothiazolin-(5,4-b)-4,6-dimethylpyridin-3-one
2-n-butylisothiazolin-(5,4-b)-4,6-diphenylpyridin-3-one
2-pentylisothiazolin-(5,4-b)-4,6-dimethylpyridin-3-one
2-hexylisothiazolin-(5,4-b)-5,6-dimethylpyridin-3-one
2-t-octylisothiazolin-(5,4-b)-5,6-dimethylpyridin-3-one
2-nonylisothiazolin-(5,4-b)-4-methylpyridin-3-one
2-dodecylisothiazolin-(5,4-b)-4,6-dimethylpyridin-3-one
2-benzyl-4,6-dimethylisothiazolo-(5,4-b)-pyridin-3-one
2-(4-methoxybenzyl)-4,6-dimethylisothiazolo-(5,4-b)-pyridin-3-one 2-(naphthalenylmethyl)-4,6-dimethylisothiazolo-
(5,4-b)-pyridin-3-one
2-propylcarbonyl-5,6-dimethylisothiazolo-(5,4-b)-
pyridin-3-one
2-isopentylcarbonyl-4,6-dimethylisothiazolo-(5,4-b)-
pyridin-3-one
2-octylcarbonyl-4-methyl, 6-ethylisothiazolo-(5,4-
b)-pyridin-3-one
2-benzoyl-4,6-dimethylisothiazolo-(5,4-b)-pyridin-
3-one
2-(3,4-dichlorobenzoyl)-4,6-dimethylisothiazolo-
(5,4-b)-pyridin-3-one
2-(4-nitrobenzoyl)-4,6-dimethylisothiazolo-(5,4-b)-
pyridin-3-one
2-(3,4,5-trimethylbenzoyl)-4,6-dimethylisothiazolo-
(5,4-b)-pyridin-3-one
2-(naphthoyl)-4,6-dimethylisothiazolo-(5,4-b)-pyri-
din-3-one
2-(2-hydroxyethyl)-4,6-diphenylisothiazolo-(5,4-b)-
pyridin-3-one
2-(diethylaminomethyl)-4,6-dimethylisothiazolo-
(5,4-b)-pyridin-3-one
2-(piperidinomethyl)-4,6-dimethylisothiazolo-(5,4-
b)-pyridin-3-one
2-(methylcarbamoyl)-4,6-dimethylisothiazolo-(5,4-
b)-pyridin-3-one
2-(n-butylcarbamoyl)-4,6-dimethylisothiazolo-(5,4-
b)-pyridin-3-one
2-(n-octylcarbamoyl)-4,6-dimethylisothiazolo-(5,4-
b)-pyridin-3-one
2-(4-phenylbutylcarbamoyl)-4,6-dimethyliso-
thiazolo-(5,4-b)-pyridin-3-one
2-[4-(4-chlorophenyl)butylcarbamoyl]-4,6-dime-
thylisothiazolo-(5,4-b)-pyridin-3-one
4,6-dimethyl-3-oxoisothiazolo-(5,4-b)-pyridin-2-yl-
carboxanilide
4,6-dimethyl-3-oxoisothiazolo-(5,4-b)-pyridin-2-yl-
4-cyanocarboxanilide
4,5,6-trimethyl-3-oxoisothiazolo-(5,4-b)-pyridin-
2-yl-4-methylcarboxanilide
4,5,6-trimethyl-3-oxoisothiazolo-(5,4-b)-pyridin-
2-yl-4-bromocarboxanilide
4,6-dimethyl-3-oxoisothiazolo-(5,4-b)-pyridin-2-yl-
4-nitrocarboxanilide
5-ethyl,6-methyl-3-oxoisothiazolo-(5,4-b)-pyridin-
2-yl-2,4,5-trichlorocarboxanilide
4,6-dimethyl-3-oxoisothiazolo-(5,4-b)-pyridin-2-yl-
3,6-dichlorocarboxanilide 4,6-dimethyl-3-oxoiso-
thiazolo-(5,4-b)-pyridin-2-yl-4-methoxycarboxani-
lide and the like.

All of the isothiazolopyridinones of this invention can be prepared by utilizing, as a starting material, a suitably substituted isothiazolo-(5,4-b)-pyridin-3(2H)-one of the formula:

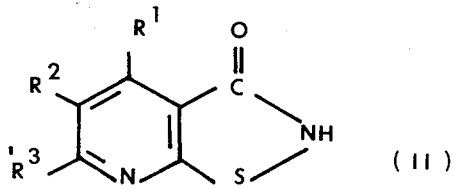

(II)

wherein R¹, R² and R³ are as previously defined.

The novel synthesis of Formula II compounds involves reacting a suitably substituted 2-mercapto-3-cyanopyridine with concentrated sulfuric acid to form the corresponding diamide disulfide, which is precipitated from solution by the addition of an alkali such as sodium hydroxide or a similar material. The insoluble disulfide is then isolated by conventional means such as filtration and dissolved in a suitable solvent such as boiling acetone, methylethyl ketone, or the like, to which anhydrous magnesium sulfate or similar material has been added.

The general reaction can be represented by the following equations:

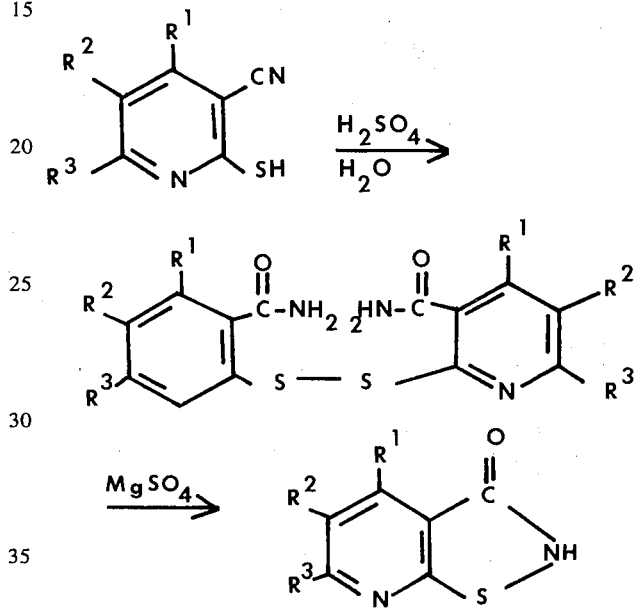

wherein R¹, R² and R³ are as previously defined.

Generally, an excess of up to 3 or more moles of concentrated sulfuric acid is employed in this reaction, which is normally conducted in the temperature range of 80° to 120°C and preferably in the range of 95° – 100°C. The preparation of substituted 2-mercapto-3-cyanopyridines is described in the literature by Schmidt and H. Kubitzek (Chem. Ber. 93 1559–65 (1966)).

The 2-aralkyl isothiazolopyridinones of this invention, can be prepared by reacting a suitably substituted isothiazolo-(5,4-b)-pyridin-3(2H)-one with a suitably substituted or unsubstituted aralkyl halide, preferably an aralkyl bromide. An acid acceptor such as a tertiary amine can be employed as a scavenger in the preparation. Representative acid acceptors include pyridine, trimethylamine and triethylamine. The reaction is advantageously carried out in an inert organic solvent, such as acetone, with a substantially equimolar ratio of reactants being preferred. Suitable solvents can be chosen from the classes of aromatic hydrocarbon, halogenated aromatic hydrocarbon, amide, ester, ketone, aliphatic hydrocarbon, ether solvents and the like. The reaction is generally conducted in a temperature range of −20°C to 80°C or more, and preferably in the range of 20° to 60°C.

The 2-acyl isothiazolopyridinones are similarly prepared by reacting a suitably substituted isothiazolo-(5,4-b)-pyridin-3(2H)-one with a suitable alkyl, aralkyl or aryl acid halide, preferably an acid bromide. Conditions such as the utilization of tertiary amines, choice of solvents, reaction temperature and molar ratios, correspond to the aralkyl halide/isothiazolopyridinone reaction described above.

The 2-carbamoyl isothiazolopyridinones can be prepared by reacting a suitably substituted isothiazolo-(5,4-b)-pyridin-3(2H)-one with an isocyanate. The reaction can be represented by the following equation:

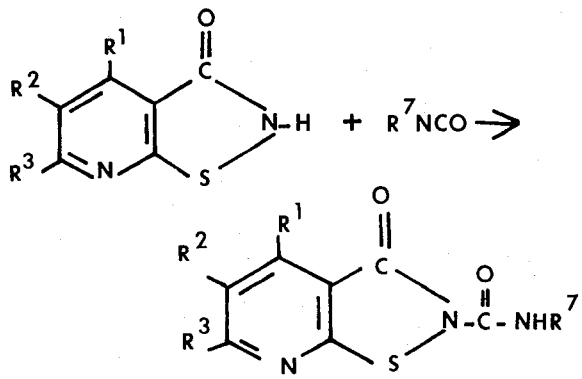

wherein $R^1$, $R^2$, $R^3$ and $R^7$ are as defined in Formula I.

Reaction conditions, including choice of solvents, temperature, molar ratios, acid acceptors and the like, correspond to the conditions described for preparing 2-aralkyl isothiazolopyridinones.

The 2-substituted isothiazolopyridinones wherein Y is the group,

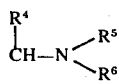

can be made by reacting a suitably substituted isothiazolo-(5,4-b)-pyridin-3(2H)-one with an aldehyde and a secondary amine in the presence of an acid catalyst, such as sulfuric acid, hydrochloric acid, or p-toluene sulfonic acid. The reaction can be represented by the following equation:

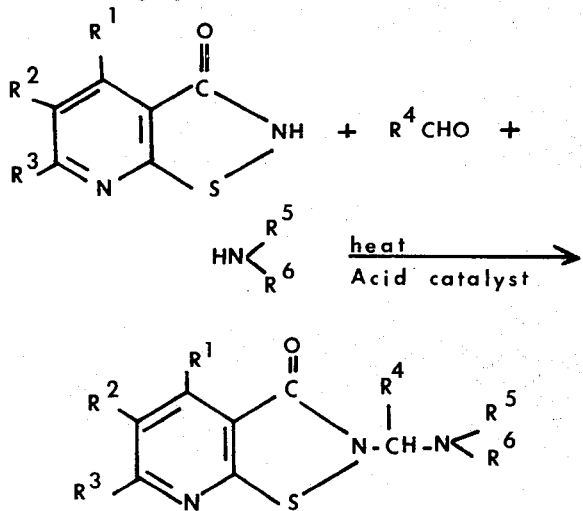

wherein $R^1$, $R^2$, $R^3$, $R^4$, $R^5$ and $R^6$ are as defined for Formula I.

Generally, an equimolar ratio of reactants is preferred but an excess of aldehyde and/or amine can be employed. The reaction can be carried out in the presence of an inert solvent such as toluene, benzene, hexane, or the like. The reaction is generally conducted in a temperature range of 70° to 150°C. and preferably in the range of 100° to 120°C.

The 2-hydroxyalkyl isothiazolopyridinones can be prepared by reacting a suitably substituted isothiazolo-(5,4-b)-pyridin-3(2H)-one with 1 mole of ethylene oxide or propylene oxide. While it is not necessary, a minute amount of catalyst such as sodium hydroxide, potassium hydroxide or p-toluene sulfonic acid can be employed. The reaction can be carried out in the presence of an inert organic solvent such as ethylene glycol, dimethyl ether, or benzene, in a temperature range of 20° – 120°C, and preferably in the range of 30°–50°C.

The 2-alkyl isothiazolopyridinones of this invention can be prepared by either of two methods. In the first procedure a suitably substituted isothiazolo-(5,4-b)-pyridin-3(2H)-one is reacted with an alkali metal hydride, such as sodium hydride, to produce the corresponding alkali metal salt of the substituted isothiazolo-(5,4-b)-pyridin-3(2H)-one which is then reacted with a suitable alkyl halide.

Generally an equimolar ratio of reactants is preferred, but an excess of alkyl halide can be employed. The reaction is advantageously carried out in an inert organic solvent selected from the classes of aromatic hydrocarbon, halogenated aromatic hydrocarbon, amide, ester, aliphatic hydrocarbon, ether solvents and the like. Suitable solvents include benzene, toluene, heptane, ethyl ether, glycol dimethyl ether and dioxane. The reaction is generally conducted in a temperature range of –20°C to 150°C or more, and preferably in the range of 20° to 100°C.

A second method of synthesizing the 2-alkyl isothiazolopyridinones involves hydrolyzing a substituted 1-H, 3-cyanopyridin-2-one of the formula:

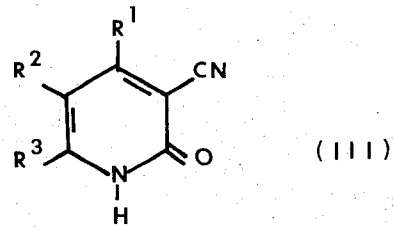

(III)

wherein $R^1$, $R^2$ and $R^3$ are as defined for Formula I, under acidic conditions to give a 1-H, 3-carboxypyridin-2-one. Aqueous organic and mineral acids are suitable for this hydrolysis. Typical of such acids are formic, acetic, hydrochloric, sulfuric and phosphoric. The reaction is normally carried out in the temperature range of 50° to 150°C. with a preferred range of 80° to 120°C. The acid derivative is then converted to the corresponding 2-chloro 3-acid chloride derivative by reaction with phosphorous oxychloride and phosphorous pentachloride. The acid chloride is in turn converted to the corresponding 3-alkylcarbamoyl derivative by reaction with a suitable alkylamine in the presence of an inert solvent such as toluene, to afford a compound having the formula:

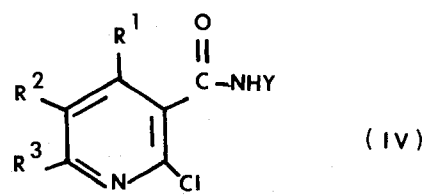

(IV)

wherein $R^1$, $R^2$ and $R^3$ are as defined in Formula I. and Y is an alkyl group as defined in Formula I. This compound is then converted to the corresponding 2-mercapto-3-alkyl-carbamoyl derivative by reaction with potassium acid sulfide (KSH). Finally, the 2-mercapto derivative is reacted with chlorine, or thionyl chloride to yield a 2-alkyl substituted isothiazolopyridinone of this invention.

The compounds of Formula III are readily prepared by methods available to those skilled in the art.

By way of demonstration the following examples are offered to illustrate this invention and are not to be construed as limitations thereof.

EXAMPLE I

Preparation of isothiazolo-(5,4-b)-4,6-dimethylpyridin-3(2H)-one

A solution of 128.5 g (0.79 m) of 3-cyano-4,6-dimethyl-2-mercaptopyridine in 300 ml concentrated sulfuric acid is heated with stirring at 95°–100°C for one hour, then cooled to 85°C. Deionized water (14.2 g. 0.89 m) is added gradually. The mixture is stirred at 65°–96°C for one-half hour, cooled to 50°C and poured over approximately one liter of crushed ice. More ice is added as needed to keep the temperature of the mixture below 50°C while the pH is adjusted to 7.4 by the addition of 50% NaOH. The insoluble material which forms is filtered off while the mixture is still warm and air dried overnight. The damp amide disulfide is dissolved in boiling acetone and anhydrous magnesium sulfate (about 200 g) is added. The mixture is filtered while still hot and the clear filtrate stripped to dryness, yielding 102.4 g. of isothiazolo-(5,4-b)-4,6-dimethyl-pyridin-3(2H)-one.

EXAMPLE II

Preparation of 2-(3,4-dichlorobenzoyl)-4,6-dimethylisothiazolo-(5,4-b)-pyridin-3-one To a stirred mixture of 9.0 g. (0.05 m) of isothiazolo-(5,4-b)-4,6-dimethylpyridin-3(2H)-one plus 5.1 g (0.05 m) of triethylamine in 200 ml reagent grade acetone is added over a period of 15 minutes, a solution of 10.5 g (0.05 m) of 3,4-dichlorobenzoyl chloride in 150 ml acetone. The temperature of the mixture increases to about 29°C and a large volume of precipitate forms. Stirring is continued for 45 minutes while the temperature drops to 24°C. Then the insoluble material is filtered off and dried to give 20.3 g of crude product which, after 3 washes with deionized water followed by one wash with acetone, weighs 13.8 g.

EXAMPLE III

Preparation of 2,4,6-trimethylisothiazolo-(5,4-b)-pyridin-3-one

To a slurry of 2.4 g (0.05 m) 50% NaH in 100 ml dried glyme there is added a total of 8.0 g (0.045 m) of 4,6-dimethyl (5,4-b)-isothiazolopyridin-3(2H)-one over a period of 45 minutes. The hydrogen which evolves is collected over water and its volume is determined to be 1,020 ml or 95% of the theoretical amount. The addition of 7.1 g (0.05 m) of methyl iodide causes no immediate observable change in the temperature or appearance of the mixture. However, after 15 minutes the color darkens, and after 3.5 hours the mixture is clear and dark brown.

After the mixture is stirred overnight at room temperature, titration of a weighed sample with N/10 hydrochloric acid shows that at least 85% of the base has reacted. The mixture is diluted with approximately 100 ml of deionized water, then transferred to a separatory funnel and 50 ml of diethyl ether is added. At this point a precipitate begins to form, so the mixture is allowed to stand at room temperature for one-half hour and then filtered. The insoluble material is washed with water and dried to give 2.0 g of a solid, m.p. 119°–121°C dec.. Another 0.8 g of the same material is obtained from the filtrate by extracting three times with ether, then recrystallizing the concentrated ether layers from ether. Total yield is 2.8 g or 32%.

EXAMPLE IV

Preparation of 2-n-butyl isothiazolin-(5,4-b)-6-methylpyridin-3-one

A mixture of 150 g (1.5 m) of 4-methoxy-3-buten-2-one, 126 g (1.5 m) of α-cyanoacetamide, and catalyst (6 cc of glacial acetic acid in 15 cc of water made basic with piperidine) in 750 cc of methyl cellosolve is refluxed and stirred for 3 hours. The solution which forms is concentrated in vacuo and the residue semi-solid is boiled in an excess of isopropanol and filtered hot. The first crop is dried to afford a 94.5 g (47%) yield of 3-cyano-6-methyl-2-pyridone, m.p. 245–246 dec. A mixture of 72 g (.537 m) of this product and 600 cc of 12N hydrochloric acid is refluxed and stirred for 6 hours. The solution is allowed to stand at room temperature for 3 days and is concentrated in vacuo. The residue solid is recrystallized with ethanol to afford a 43 g (52.5%) yield of 1H, 3-carboxy-6-methylpyridin-2-one, m.p. 226°.

To a solution of 71.5 g (.464 m) of this product (combining two preparations) in 150 cc of phosphorous oxychloride is added slowly, 96.5 g (.464 m) of phosphorous pentachloride. The solution which forms is refluxed and stirred for 3½ hours, allowed to stand at room temperature for 18 hours, and concentrated in vacuo. To an oil suspension of the concentrate in 200 cc of toluene is added dropwise 101.5 g (1.39 m) of n-butylamine. The resulting solution is poured into an equal volume of water. The organic layer is dried over magnesium sulfate and concentrated in vacuo to afford a 59 g (56%) yield of 2-chloro-6-methylpyridine-3-(N-n-butyl)carboxamide, an oil. To a solution of 59 g (.26 m) of this oil in 200 cc of methyl cellosolve is added a hydrogen sulfide saturated solution of 33.6 g (.52 m) 87% potassium hydroxide pellets in 200 cc of methyl cellosolve (KSH prep.). The solution is refluxed and stirred for 4 hours and allowed to stand at room temperature for 3 days. The solution is concentrated in vacuo and the residue is dissolved in an excess of water and acidified with glacial acetic acid. The suspension which forms is vacuum filtered and the first crop recrystallized with isopropanol to afford a 27.5 g (47%) yield of 2-mercapto-6-methyl-pyridine-3(N-n-butyl)-carboxamine, m.p. 165°–67°.

To an ice cooled solution of 25.2 g. (.1125 m) of said product in 200 cc of chloroform is added dropwise a solution of 8.4 g (.118 m) chlorine in 100 cc of chloroform. The solution is steam heated for 2 hours and is neutralized with aqueous sodium bicarbonate. The organic layer is concentrated in vacuo and the residue oil is vacuum distilled to afford a 44% yield of 2-n-butyl isothiazolin-(5,4-b)-6-methylpyridin-3-one, BP 130°/.2mm.

EXAMPLE V

Preparation of 2-benzyl-4,6-dimethylisothiazolo-(5,4-b)-pyridin-3-one

Triethylamine (approximately 3 ml) is added to a slurry of 5.0 g of 4,6-dimethylisothiazolo-(5,4-b)-pyridin-3(2H)-one in 120 ml reagent grade acetone until the mixture becomes homogeneous. A solution of 4.0 g (0.024 m) of benzyl bromide in 20 ml acetone is then added. The reaction mixture is stirred for 3 days at room temperature and is then stripped to dryness. The residue is washed once with deionized water, then with 95% 2B ethanol, then ether and dried to give the product.

EXAMPLE VI

Preparation of 4,6-dimethyl-3-oxoisothiazolo-(5,4-b)-pyridin-2-yl-2,5-dichlorocarboxanilide To a stirred solution of 20.0 g (0.11 m) isothiazolo-(5,4-b)-4,6-dimethylpyridin-3(2H)-one in one pint (473 ml) of reagent grade acetone is added, 20.9 g (0.11 m) of 2,5-dichlorophenylisocyanate dissolved in 100 ml acetone. A large volume of precipitate forms almost immediately and more acetone (approximately 200 ml) is added. An increase of a few degrees Centigrade is observed in the mixture. Stirring is continued overnight at room temperature. The insoluble material is then filtered off, washed with acetone and dried to give 34.8 g of the product.

EXAMPLE VII

Preparation of 2-morpholinomethyl-4,6-dimethylisothiazolo-(5,4-b)-pyridin-3-one

Eighteen grams (0.1 m) of 4,6-dimethylisothiazolo-(5,4-b)-pyridin-3-one, 93 grams (0.5 m) of N,N'-bis(morpholino)-methane, and two drops of 35% aqueous hydrochloric acid are heated on a steam bath for 16 hours. The material is then heated to 125°C at reduced pressure (1 mm. of mercury) to remove morpholine and excess N,N'-bis (morpholino)-methane. The residue, weighing 26 grams is the desired 2-morpholinomethyl-4,6-dimethyl-isothiazolo-(5,4b-pyridin-3-one).

EXAMPLE VIII

Preparation of 2-(2-hydroxyethyl)-4,6-dimethylisothiazolo-(5,4-b)-pyridin-3-one

A slurry of 36 grams (0.2 m) of isothiazolo-(5,4-b)-4,6-dimethylpyridin-3(2H)-one in 100 ml of ethylene glycol dimethyl ether is heated under reflux (about 80°C) while passing in a slow stream of ethylene oxide. After 48 hours the solvent is removed by evaporation. The weight gain is found to be 8.0 grams, corresponding to 0.18 mols of ethylene oxide. The product is mainly 2-(2-hydroxyethyl)-4,6-dimethyl-isothiazolo-(5,4-b)-pyridin-3-one.

EXAMPLE IX

In a manner similar to that of Examples 1 to 8, the following compounds are likewise readily prepared:
isothiazolo-(5,4-b)-4,6,diethylpyridin-3(2H)-one
2-propylisothiazolin-(5,4-b)-6-isobutylpyridin-3-one
2-dodecylisothiazolin-(5,4-b)-4,6-dimethylpyridin-3-one
2-(4-methoxybenzyl)-4,6-dimethylisothiazolo-(5,4-b)-pyridin-3-one
2-propylcarbonyl-5,6-dimethylisothiazolo-(5,4-b)-pyridin-3-one
2-(4-nitrobenzoyl)-4,6-dimethylisothiazolo-(5,4-b)-pyridin-3-one
2-hydroxymethyl-4,6-dimethylisothiazolo-(5,4-b)-pyridin-3-one
2-(piperidinomethyl)-4,6-dimethylisothiazolo-(5,4-b)-pyridin-3-one
4,6-dimethyl-3-oxoisothiazolo-(5,4-b)-pyridin-2-yl-4-nitrocarboxanilide
5-ethyl,6-methyl-3oxoisothiazolo-(5,4-b)-pyridin-2-yl, 2,4,5-trichlorocarboxanilide The novel isothiazolopyridinones and salts of this invention are biocidally active compounds, and as such, are suitable for the control of living organisms and particularly microorganisms such as phytopathogenic fungi. Fungicidal evaluation of the isothiazolopyridinones of this invention was carried out by way of a preliminary foliar screening test. The general procedure for the fungicidal test is to take potted plants in proper condition of growth for susceptibility to the plant diseases to be evaluated, to spray these on a moving belt and to allow them to dry. The plants are then inoculated with the respective fungal spores and allowed to incubate until the disease symptoms and the disease control are read or estimated. Percentage of disease control is recorded.

The compounds of the present invention were tested at a concentration of 300 ppm in a solution or suspension made by dissolving a weighed amount of the candidate fungicide in a 50:50 mixture of acetone and methanol and then adding an equal volume of water.

Plant diseases controlled by the compounds of this invention include botrytis blight (*Botrytis cinerea*), rice blast (*Piricularia oryzae*), tomato late blight (*Phytophthora infestans*), barley helminthosporium (*Helminthosporium teres*), celery cercospora blight (*Cercospora apii*), grape downy mildew (*Plasmopara viticola*), and wheat leaf rust (*Puccinia recondita*).

Further antimicrobial evaluation of the representative compounds revealed their utility in controlling such microorganisms as *Rhizopus stolonifer*, *Aspergillus niger*, *Rhodotorula rubra*, *Staphylococcus aureus* and *Escherichia coli*.

Selected isothiazolopyridinones also demonstrated pesticidal activity against various mites, ticks, nematodes, and corn rootworm larvae. Other compounds demonstrated post emergence herbicidal activity.

Generally, control of a living organism is achieved in accordance with this invention by contacting the organism with an isothiazolopyridinone in an amount which is effective to control said organism. Any of the techniques known in the art may be employed to disseminate the isothiazolopyridinone in a manner so as to achieve the desired contact with the organism to be controlled. Spraying, painting, immersing and fumigating are typical of such techniques.

In general, a locus subject to attack by microorganisms may be protected in accordance with this invention by incorporating into said locus an isothiazolopyridinone in an amount which is effective to control said microorganisms. The exact amount of isothiazolopyridinone required will, of course, vary with the medium being protected, the microorganisms being controlled, the particular compositions thereof being employed and the like.

The term "control" as employed in the specification and claims of this application is to be construed as any means which adversely affects the existence or growth of any microorganism or living organism. Such means may comprise a complete killing action, eradication, arresting in growth, inhibition, reduction in number or any combination thereof.

The isothiazolopyridinones of this invention are especially useful as agricultural fungicides. As such, they are particularly valuable when formulated in a fungicidal composition. Such compositions normally comprise an agronomically acceptable carrier and the compounds disclosed herein as the active agent or agents. Where necessary or desirable, surfactants or other additives may be incorporated to give uniformly formulated mixtures. By "agronomically acceptable carrier" is meant any substance which can be utilized to dissolve, disperse or diffuse the chemical incorporated therein without impairing the effectiveness of the toxic agent and which does no permanent damage to such environment as soil, equipment and agronomic crops.

For use as pesticides, the compounds of this invention are usually taken up in an agronomically acceptable carrier or formulated so as to render them suitable for subsequent dissemination. For example, the isothiazolopyridinones may be formulated as wettable powders, emulsion concentrates, dusts, granular formulations, aerosols or flowable emulsifiable concentrates. In such formulations, the isothiazolopyridinones are extended with a liquid or solid carrier and, when desired, suitable surfactants are likewise incorporated.

Compounds of this invention may be dissolved in a water-miscible liquid, such as ethanol, isopropanol, acetone, and the like. Such solutions are easily extended with water.

The isothiazolopyridinones may be taken up on or mixed with a finely particled solid carrier, as for example, clays, inorganic silicates, carbonates, and silicas. Organic carriers may also be employed. Dust concentrates are commonly made wherein the isothiazolopyridinones are present in the range of 20 to 80%. For ultimate applications these concentrates are normally extended with additional solid from about 1 to 20%.

Wettable powder formulations are made by incorporating the compounds of this invention in an inert, finely divided solid carrier along with a surfactant which may be one or more emulsifying, wetting, dispersing, or spreading agents or blend of these. The isothiazolopyridinones are usually present in the range of 10 to 80% by weight and the surfactants in from 0.5 to 10% by weight. Commonly used emulsifying and wetting agents include polyoxyethylated derivatives of alkylphenols, fatty alcohols, fatty acids and alkylamines; alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the isothiazolopyridinone toxicant onto the solid carrier by means of a volatile solvent, such as acetone. In this manner, adjuvants, such as activators, adhesives, plant nutrients, synergists and various surfactants, may also be incorporated.

Emulsifiable concentrate formulations may be prepared by dissolving the isothiazolopyridinones of this invention in an agronomically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents are commonly employed. The surfactants useful as emulsifying agents may constitute about 0.5 to 10% by weight of the emulsifiable concentrate and may be anionic, cationic or nonionic in character. Anionic surfactants include alcohol sulfates or sulfonates, alkylarene sulfonates and sulfosuccinates. Cationic surfactants include n-alkyl amine salts and quaternaries with one or more n-alkyl groups. Nonionic emulsifying agents include ethylene oxide adducts of alkylphenols, fatty alcohols, mercaptans and fatty acids. The concentration of the active ingredients may vary from 10 to 80%, preferably in the range of 25 to 50%.

For use as phytopathogenic agents, these compounds should be applied in an effective amount sufficient to exert the desired biocidal activity by techniques well known in the art. Usually, this will involve the application of the isothiazolopyridinones to the loci to be protected in an effective amount when incorporated in an agronomically acceptable carrier. However, in certain situations it may be desirable and advantageous to apply the compounds directly onto the loci to be protected without the benefit of any substantial amount of carrier. This is a particularly effective method when the physical nature of the isothiazolopyridinone is such as to permit what is known as "low-volume" application, that is, when the compounds are in liquid form or substantially soluble in higher boiling solvents.

The application rate will, of course, vary depending upon the purpose for such application, the isothiazolopyridinones being utilized, the frequency of dissemination and the like.

For use as agricultural fungicides, dilute sprays may be applied at concentrations of 0.05 to 20 pounds of the active isothiazolopyridinone ingredient per 100 gallons of spray. They are usually applied at 0.1 to 10 pounds per 100 gallons and preferably at 0.125 to 5 pounds per 100 gallons. In more concentrated sprays, the active ingredient is increased by a factor of 2 to 12. With dilute sprays, applications are usually made to the plants until run-off is achieved, whereas with more concentrated or low-volume sprays the materials are applied as mists.

The compounds of this invention may be utilized as the sole biocidal agents or they may be employed in conjunction with other fungicides, bactericides, algaecides, insecticides, miticides and comparable pesticides.

We claim:
1. A compound of the formula:

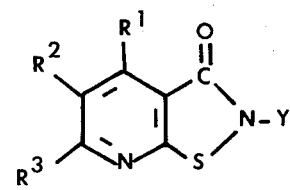

wherein Y is hydrogen; $(C_1-C_{12})$ alkyl; unsubstituted aralkyl of up to 11 carbon atoms; aralkyl of up to 11 carbon atoms substituted with halogen, cyano, nitro, $(C_1-C_4)$ alkoxy or $(C_1-C_6)$ alkyl; $(C_1-C_4)$ alkylcarbonyl; $(C_6-C_{10})$ unsubstituted arylcarbonyl; $(C_6-C_{10})$ arylcarbonyl substituted with halogen, cyano, nitro, $(C_1-C_4)$ alkoxy or $(C_1-C_6)$ alkyl; unsubstituted aralkylcarbonyl of up to 11 carbon atoms; aralkylcarbonyl of up to 11 carbon atoms substituted with halogen, cyano, nitro, $(C_1-C_4)$ alkoxy or $(C_1-C_6)$ alkyl; $(C_2-C_3)$ hydroxyalkyl; a group of the formula:

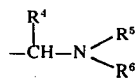

wherein $R^4$ is hydrogen, $(C_1-C_3)$ alkyl or phenyl and $R^5$ and $R^6$ are individually $(C_1-C_4)$ alkyl or taken together with the nitrogen atom to which they are attached, form a morpholino or piperidino group; or a carbamoyl group of the formula:

wherein $R^7$ is $(C_1-C_{18})$ alkyl; unsubstituted $(C_6-C_{10})$ aryl; $(C_6-C_{10})$ aryl substituted with halogen, cyano, nitro, $(C_1-C_4)$ alkoxy, or $(C_1-C_6)$ alkyl; unsubstituted aralkyl of up to 11 carbon atoms or aralkyl of up to 11 carbon atoms, substituted with halogen, cyano, nitro, $(C_1-C_4)$ alkoxy, or $(C_1-C_6)$ alkyl;

$R^1$ and $R^3$ are individually hydrogen, $(C_1-C_4)$ alkyl, phenyl, or benzyl; and $R^2$ is hydrogen or $(C_1-C_4)$ alkyl; provided that at least one of $R^1$, $R^2$, and $R^3$ is other than hydrogen.

2. A compound according to claim 1 wherein $R^2$ is hydrogen and $R^1$ and $R^3$ are $(C_1-C_4)$ alkyl groups.

3. A compound according to claim 2 wherein $R^1$ and $R^3$ are methyl groups.

4. A compound according to claim 3 wherein Y is a methyl group.

5. A compound according to claim 3 wherein Y is an unsubstituted $(C_6-C_{10})$arylcarbamoyl group.

6. A compound according to claim 5 wherein Y is a phenylcarbamoyl group.

7. A compound according to claim 3 wherein Y is a $(C_6-C_{10})$ arylcarbamoyl group substituted with halogen, cyano, nitro, $(C_1-C_4)$ alkoxy or $(C_1-C_6)$ alkyl.

8. A compound according to claim 3 wherein Y is a $(C_6-C_{10})$ arylcarbonyl group substituted with halogen, cyano, nitro, $(C_1-C_4)$ alkoxy or $(C_1-C_6)$ alkyl.

9. A compound according to claim 7 wherein Y is a 4-methoxyphenylcarbamoyl group.

10. A compound according to claim 3 wherein Y is a $(C_1-C_8)$ alkylcarbamoyl group.

11. A compound according to claim 8 wherein Y is a n-butylcarbamoyl group.

12. A compound according to claim 3 wherein Y is an unsubstituted aralkyl group of up to 11 carbon atoms.

13. A compound according to claim 12 wherein Y is a benzyl group.

14. A compound according to claim 3 wherein Y is an unsubstituted $(C_6-C_{10})$ arylcarbonyl group.

15. A compound according to claim 14 wherein Y is a benzoyl group.

16. A compound according to claim 8 wherein Y is a 3,4-dichlorobenzoyl group.

17. A process for preparing an isothiazolopyridinone of the formula:

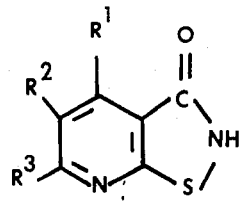

wherein $R^1$ and $R^3$ are each hydrogen, $(C_1-C_4)$ alkyl, phenyl or benzyl; and $R^2$ is hydrogen or $(C_1-C_4)$ alkyl provided that, at least one of $R^1$, $R^2$ and $R^3$ is other than hydrogen, which comprises:

a. reacting in the temperature range of 80°–120°C., a substituted 2-mercapto-3-cyanopyridine of the formula:

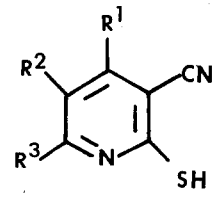

wherein $R^1$, $R^2$, and $R^3$ are as defined above, with an excess of concentrated sulfuric acid to form the corresponding diamide disulfide of the formula:

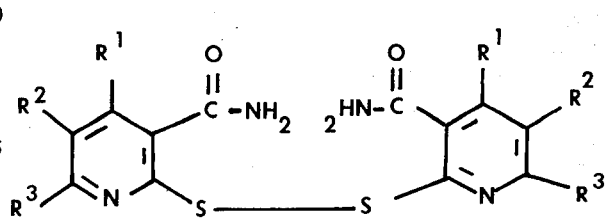

wherein $R^1$, $R^2$, and $R^3$ are as defined above;

b. precipitating the disulfide by neutralization with an alkali;

c. isolating the disulfide from the reaction mixture; and d. contacting a ketonic solution of the diamide disulfide with anhydrous magnesium sulfate to produce the isothiazolopyridinone.

18. A process according to claim 17 which comprises a. reacting the 2-mercapto-3-cyanopyridine with the sulfuric acid in the temperature range of 95° to 100°C.;

b. precipitating the resultant product by neutralization with an alkali;

c. filtering off the diamide disulfide and d. heating the diamide disulfide in refluxing acetone in the presence of magnesium sulfate.

* * * * *